(12) United States Patent  
Kang et al.

(10) Patent No.: US 9,131,972 B2  
(45) Date of Patent: Sep. 15, 2015

(54) SCREW FOR FIXING VERTEBRA

(71) Applicant: L & K BIOMED CO., LTD., Seoul (KR)

(72) Inventors: Gook-Jin Kang, Seoul (KR); Choon-Sung Lee, Seoul (KR)

(73) Assignee: L&K Biomed Co., Ltd., Seoul (KR)

( * ) Notice: Subject to any disclaimer, the term of this patent is extended or adjusted under 35 U.S.C. 154(b) by 255 days.

(21) Appl. No.: 13/689,019

(22) Filed: Nov. 29, 2012

(65) Prior Publication Data

US 2013/0138162 A1    May 30, 2013

(30) Foreign Application Priority Data

Nov. 30, 2011   (KR) .......................... 10-2011-0126897

(51) Int. Cl.  
*A61B 17/86* (2006.01)  
*A61B 17/70* (2006.01)

(52) U.S. Cl.  
CPC ......... *A61B 17/8605* (2013.01); *A61B 17/7032* (2013.01); *A61B 17/7037* (2013.01)

(58) Field of Classification Search  
CPC ........... A61B 17/7037; A61B 17/7032; A61B 17/8605  
USPC .................................................. 606/268–270  
See application file for complete search history.

(56) References Cited

U.S. PATENT DOCUMENTS

2007/0118117 A1\* 5/2007 Altarac et al. .................. 606/61

\* cited by examiner

*Primary Examiner* — Andrew Yang  
(74) *Attorney, Agent, or Firm* — Kramer Amado, P.C.

(57) ABSTRACT

A screw for fixing vertebra for letting a patient perform spinal motion more smoothly after a pedicle screw insertion surgery is disclosed. A head portion of the screw body is pivotally joined in sliding contact on the head seat portion of a movable washer, which is also pivotally joined in sliding contact on the washer seat portion of a fastening nut. A first aperture and a second aperture are formed in the fastening nut and movable washer respectively, and an elongating portion without a thread is formed between a screw portion and the head portion of the screw body.

5 Claims, 7 Drawing Sheets

SCREW FOR FIXING VERTEBRA

CROSS REFERENCE TO RELATED APPLICATION

This application claims priority to Korean Patent Application No. 10-2011-0126897 filed on Nov. 30, 2011 in the Korean Intellectual Property Office, the entire disclosure of which is incorporated herein by reference.

BACKGROUND OF THE INVENTION

1. Field of the Invention

The present invention relates to a screw for fixing vertebra, and more specifically, to a screw for fixing vertebra for giving various option, for screw insertion, to an operator with maintaining condition of lower profile screw.

2. Description of the Related Art

In general, spinal diseases include prolapsed intervertebral disk (spinal disk) and spinal scoliosis, and a patient with part of the spine damaged cannot engage in activities necessary for daily life in such a condition. Even if the extent of damage is not so serious, if the damaged part of the spine is pressed or touched by another adjacent part it may cause pain. Due to uneven division of various loads applied to the human body, pain is induced or a degenerative disease is brought about.

Therefore, a patient with part of the spine broken or damaged cannot lead a stable daily life unless the damaged part is corrected by carrying out a surgery for supporting it by using an artificial aid in the damaged part.

Of such spinal diseases, spinal scoliosis is a disease in which vertebrae are bent and twisted. If the spinal scoliosis is left alone, deformation of the spine progresses to eventually bring about serious deformity, followed by complications such as deformation of internal organs.

Such spinal scoliosis can be cured completely by wearing a brace or surgery according to the bent angle of vertebrae. In the methods of operating on spinal scoliosis, there is a method known as a pedicle screw inserting technique for correcting by inserting screws into bent vertebrae.

The pedicle screw inserting technique is a method for helping the spine recover to a normal condition by inserting pedicle screws into bent vertebrae and connecting the pedicle screws with each other using a rod.

However, in the case of screws for fixing vertebra used in the conventional pedicle screw insertion surgery, the degree of freedom between the screw body driven into and fixed to the vertebra and the fastening screw for fixing the connecting rod is so low that it is not possible to move in a desired angle range. Therefore, there is a problem that it is difficult for the operator to perform a fixing operation within a desired range early during an operation and after performing the pedicle screw insertion surgery there are considerable constraints for the patient to perform spinal motion.

SUMMARY OF THE INVENTION

Accordingly, is an object of the present invention to provide a screw for fixing vertebra whereby the patient can perform spinal motion more comfortably by letting the fastening screw for fixing the connecting rod move with a degree of freedom within a smoother and wider angle range from the screw body driven into and fixed to the vertebra with maintaining condition of lower profile screw.

In order to accomplish the foregoing object, according to an embodiment of the present invention, there is provided a screw for fixing vertebra including: a screw body having a screw portion driven into and fixed to the vertebra and a spherical head portion formed at the top end of the screw portion; a movable washer, which includes a head seat portion formed therein so that the head portion of the screw body is mounted thereon after the screw portion of the screw body is inserted therein, and in which the screw body is pivotally joined therein in sliding contact between the head portion and the head seat portion; a fastening nut which includes an insertion hole formed therein to insert and pass the screw body, a washer seat portion formed below the insertion hole so that the movable washer is pivotally mounted thereon in sliding contact between the movable washer and the washer seat portion, and a rod fastening groove which extends from the upper side of the washer seat portion to the top end of the fastening nut; and a clamping bolt which includes a male thread formed thereon to be screwed into an upper portion of the insertion hole of the fastening nut, so as to press and fix a connecting rod inserted through the rod fastening groove of the fastening nut.

Preferably, the fastening nut includes a first aperture formed with a sloping face whose width gradually widens as it goes downward from the lower portion of the washer seat portion, and a bottom end portion of the head seat portion of the movable washer is protruded out of the fastening nut through the first aperture of the fastening nut.

Preferably, a height of the bottom end portion of the movable washer exposed downward of the fastening nut through the first aperture is equal to the height of the first aperture.

Preferably, the movable washer has a second aperture formed with a sloping face whose width widens gradually as it goes downward from the lower portion of the head seat portion.

Preferably, the screw portion of the screw body includes a thread formed thereon from the bottom end thereof, and an elongating portion which elongates between the thread and the head portion and does not have a thread formed thereon.

Preferably, a first tool insert groove for inserting a tool is formed in the top end portion of the head portion of the screw body, and a shaking prevention groove communicating with the first tool insert groove is formed at the center of the head portion of the screw body.

Preferably, a length of the elongating portion is equal to the sum of a length of the sloping face of the first aperture of the fastening nut and a length of the sloping face of the second aperture of the movable washer.

According to the above-mentioned screw for fixing vertebra of the present invention, the head portion of the screw body is pivotally joined in sliding contact on the head seat portion of a movable washer, which is again pivotally joined in sliding contact on the washer seat portion of a fastening nut. Therefore, the fastening nut can move more smoothly with respect to the screw body. Accordingly, the motion between the vertebras fixed to each other by the connecting rod can be made more comfortably and naturally.

In addition, as mentioned above, the first aperture and the second aperture are formed in the fastening nut and movable washer respectively, and an elongating portion without a thread is formed between the screw portion and the head portion of the screw body, so that the fastening nut can move with a greater degree of freedom within the maximum allowable angle range defined by the sloping face of the first aperture. Accordingly, it is possible to more effectively increase the degree of freedom with respect to the motion between vertebras fixed to each other by the connecting rod.

BRIEF DESCRIPTION OF THE DRAWINGS

The above objects, features and advantages of the present invention will become more apparent to those skilled in the related art in conjunction with the accompanying drawings. In the drawings.

DETAILED DESCRIPTION

Figure 1:
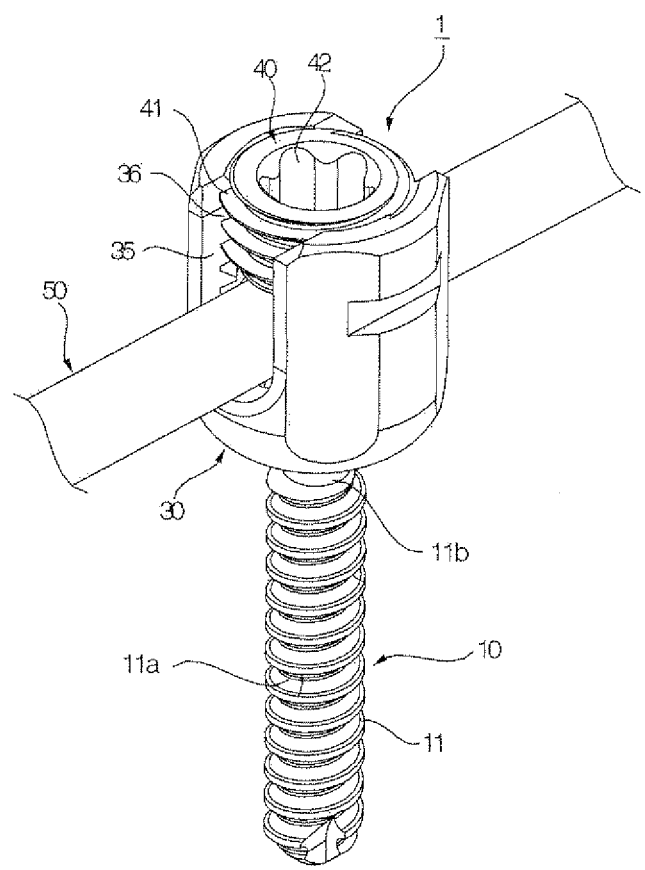
FIG. 1 is a perspective view showing a screw for fixing vertebra according to an embodiment of the present invention.

Hereinafter, some embodiments of the present invention will be described in detail with reference to the accompanying drawings.

When inserting reference numerals into the constituents in the respective drawings, although the constituents are shown in different drawings, so far as the constituents are the same, they are described to have the same reference numeral, where possible. The detailed description for the well-known function and constitution, judged to make the gist of the invention obscure, will be omitted.

Figure 2:
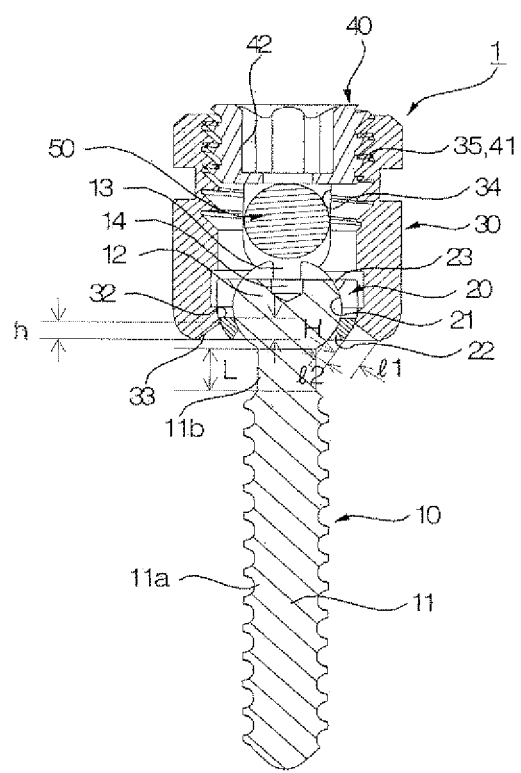
FIG. 2 is a cross sectional view of the screw for fixing vertebra shown in FIG. 1.

FIG. 1 is a perspective view showing a screw for fixing vertebra according to an embodiment of the present invention, and FIG. 2 is a cross sectional view of a screw for fixing vertebra shown in FIG. 1.

Referring to FIGS. 1 and 2, the screw for fixing vertebra 1 of the present embodiment includes a screw body 10, a movable washer 20 in which one end of the screw body 10 is pivotally joined, a fastening nut 30 for containing the movable washer 20 therein, and a clamping bolt 40 screwed with the fastening nut 30.

Figure 3:
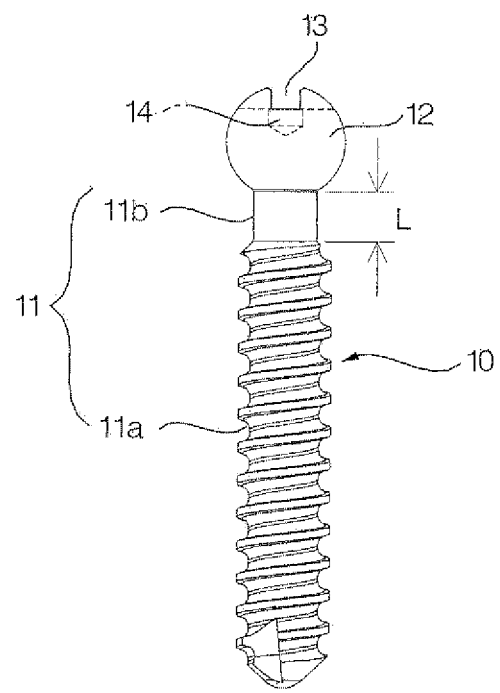
FIG. 3 is a side view showing a screw body separated from the screw for fixing vertebra shown in FIG. 2.

FIG. 3 is a side view showing the screw body separated from the screw for fixing vertebra shown in FIG. 2.

Referring to FIG. 3, the screw body 10 has a screw portion 11 in which the thread is formed thereon from the lower end portion thereof so as to be driven into and fixed to the vertebra and a spherical head portion 12 which is formed at the top end portion thereof.

Meanwhile, the screw portion 11 includes a thread 11a formed on the outer circumferential surface thereof and an elongating portion 11b which elongates between the thread 11a and the head portion 12 and which has no thread formed thereon.

Thus, by forming the elongated portion 11b without a thread between the thread 11a and the head portion 12 of the screw portion 11, it is possible to prevent interference with a sloping face 33a of a first aperture 33 of the fastening nut 30 to be described later. Therefore, the screw body 10 is allowed to be operated with a greater degree of freedom in a wider angle range.

Meanwhile, it is preferable that the length L of the elongating portion 11b be formed equal to the sum of the length 11 of the sloping face 33a defined in the first aperture 33 of a fastening nut 30 to be described later and the length 12 of the sloping face of the second aperture 22 of the movable washer 20.

In addition, a first cross-shaped tool insert groove 13 that enables the screw body 10 to be driven into and fixed to the vertebra using a tool such as an electric drill is formed in the head portion 12 of the screw body 10.

In the course of driving the screw body 10 into the vertebra for fixing thereto using a tool, it is necessary to prevent vibration of the screw body 10. For this purpose, a shaking prevention groove 14 for preventing the occurrence of the shaking of the screw body 10 is formed in the central portion of the screw portion 11 of the screw body 10. The shaking prevention groove 14 communicates with the first tool insert groove 13.

Figure 4:
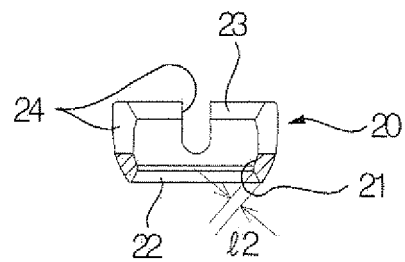
FIG. 4 is a cross sectional view showing a movable washer separated from the screw for fixing vertebra shown in FIG. 2.

FIG. 4 is a cross sectional view showing the movable washer separated from the screw for fixing vertebra shown in FIG. 2.

Referring to FIG. 4, a head seat portion 21 is formed in the inner central portion of the movable washer 20. After the screw portion 11 of the screw body 10 passes through vertically and is inserted into the movable washer 20, the head portion 12 is placed on the head seat portion 21.

The head seat portion 21 has a cross section of a curved surface groove shape corresponding to the outer circumferential surface of the head portion 12. Thus, in a state of sliding contact with the outer circumferential surface of the head portion 12 of the screw body 10, the screw body 10 is mounted pivotally on the head seat portion 21 of the movable washer 20.

Meanwhile, an insert portion 23 for guiding to be inserted into the head portion 12 of the screw body 10 is formed at upper side of the head seat portion 21. The insert portion 23 has a cross section shape sloped downward for engagement with the head portion 12. A second aperture 22 is formed in the opposite lower portions of the insert portion 23.

Further, four slits 24 are formed on the side wall of the movable washer 20 at equal intervals in the circumferential direction. When the movable washer 20 is inserted into the fastening nut 30, a washer seat portion 32 formed in the fastening nut 30 to be described later is inserted into and fixed on these slits 24. The slits 24 play a role of imparting elastic deformation to the movable washer 20 so that the head portion 12 of the screw body 10 is more easily inserted into and mounted on the head seat portion 21 when the screw body 10 is inserted through the insert portion 23. The slits 24 are formed from the upper side of the head seat portion 21 to the top end of the movable washer 20, and the upper portion is open.

Figure 5:
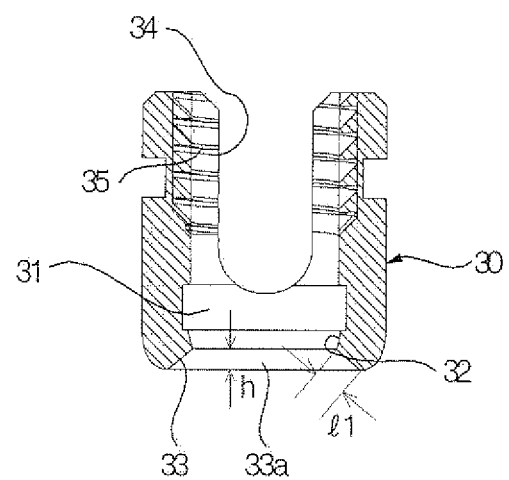
FIG. 5 is a cross sectional view showing a fastening nut separated from the screw for fixing vertebra shown in FIG. 2.

FIG. 5 is a cross sectional view showing the fastening nut separated from the screw for fixing vertebra shown in FIG. 2.

Referring to FIG. 5, the fastening nut 30 includes an insertion hole 31 penetrated vertically therein, a washer seat portion 32 of a curved groove shape which is formed below the insertion hole 31 so that the movable washer 20 is pivotally mounted thereon in sliding contact, and a rod fastening groove 34, which extends from the upper side of the washer seat portion 32 to the top end of the fastening nut 30, the upper portion of which is formed in an open shape on both sidewalls of the fastening nut 30 that face each other. A connecting rod is inserted and fixed in the rod fastening groove 34.

Meanwhile, a female thread 35 screwed to a male thread of the clamping bolt 40 is formed on the inner circumferential wall of the fastening nut 30. The female thread 35 is formed on the upper portion of the insertion hole 31 in which the rod fastening groove 34 of open shape is formed.

Figure 6:
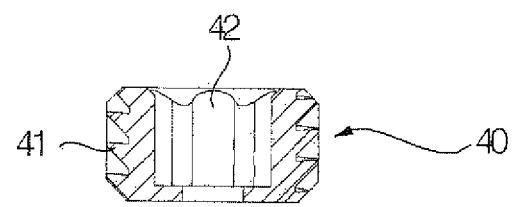
FIG. 6 is a cross sectional view showing a clamping bolt separated from the screw for fixing vertebra shown in FIG. 2.
Figure 7A:
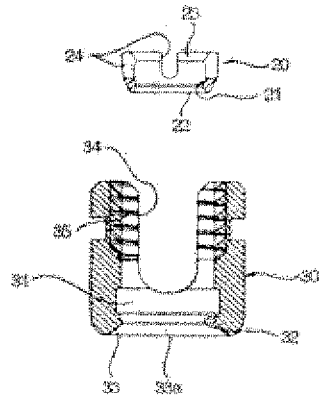
FIGS. 7(a), 7(b), 7c and 7(d) are sequential views for describing the fastening processes of the screw for fixing vertebra according to an embodiment of the present invention.
Figure 7B:
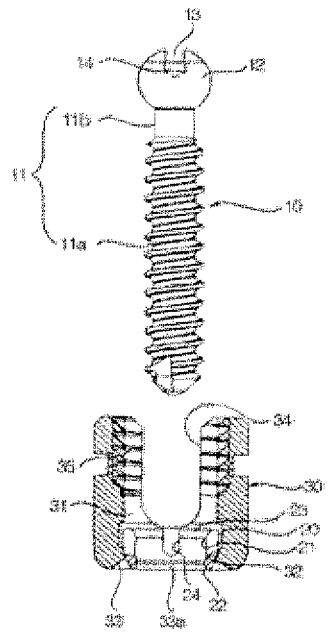
Figure 7C:
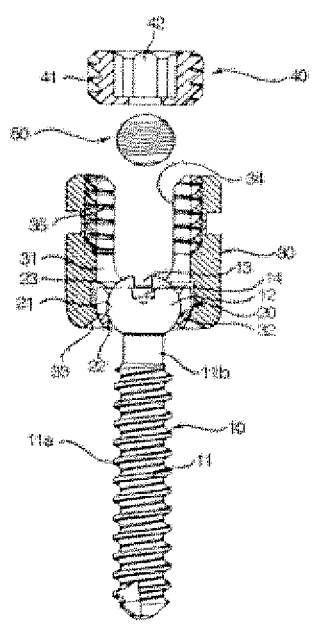
Figure 7D:
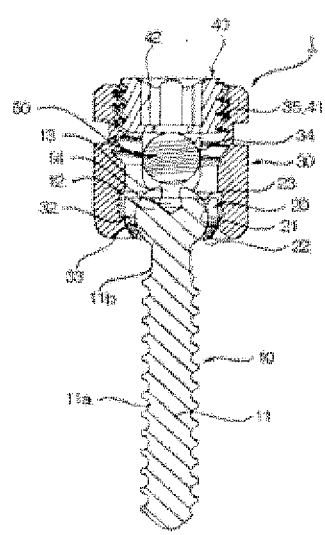

FIG. 6 is a cross sectional view showing the clamping bolt separated from the screw for fixing vertebra shown in FIG. 2.

Referring to FIG. 6, the clamping bolt 40 includes a male thread 41, which is formed on the outer circumferential surface and is inserted into the insertion hole 31 of the fastening nut 30 to be screwed to the female screw 35 of the fastening nut 35, and a second tool insert groove 42, which is formed to a predetermined depth from the top surface of the clamping bolt 40, and clamp-fixes the connecting rod 50 that is inserted along a rod fastening groove 34 of the fastening nut 30 by inserting a tool such as a wrench.

FIG. 7(*a*) to (*d*) are sectional views showing the fastening sequence of the screw for fixing vertebra according to an embodiment of the present invention.

To describe the assembly process of the screw for fixing vertebra 1 of the present embodiment with reference to FIG. 7, first the movable washer 20 is inserted into the insertion hole 31 of the fastening nut 30. At this time, the bottom end of the movable washer 20 is placed and mounted on the washer seat portion 32 of the fastening nut 30.

Next, the screw body 10 is inserted into the fastening nut 30 and the movable washer 20. At this time, the screw body 10 passes through the inside of the movable washer 20 to be inserted, with the head portion 12 placed and mounted on the washer seat portion 32.

Then, a tool is inserted and passed through the insertion hole 31 of the fastening nut 30, so that the front end portion of the tool is inserted into the first tool insert groove 13 and the shaking prevention groove 14 of the screw body 10. After that, the tool is operated so that the thread 11*a* of the screw body 10 is driven into and fixed to the vertebra.

In addition, the connecting rod 50 that is inserted by passing through the rod fastening groove 34 of the fastening nut 30 is clamped and fixed by the clamping bolt 40.

In the screw for fixing vertebra 1, in order to achieve spinal motion of more various and smooth types, it is very important that the fastening nut 30 fixed with the connecting rod 50 can move with a greater degree of freedom with respect to the screw body 10 driven into and fixed to the vertebra.

For this purpose, the fastening nut 30 of the screw for fixing vertebra 1 of the present embodiment includes the first aperture 33 formed with a sloping face whose width widens as it goes downward from the lower portion of the washer seat portion 32.

Referring to FIG. 2 again, the bottom end portion of the head seat portion 21 of the movable washer 20 is fastened so as to be exposed downward of the fastening nut 30 to be protruded through the first aperture 33 of the fastening nut 30.

At this time, it is preferable that the depth h of the bottom end portion of the movable washer 20 that is protruded downward of the fastening nut 30 through the first aperture 33 be formed equal to the height H of the first aperture 33 of the fastening nut 30.

Further, the movable washer 20 includes a second aperture 22 that is formed with a sloping face whose width widens gradually as it goes downward from the lower portion of the head seat portion 21.

Accordingly, the fastening nut 30 and the movable washer 20 are provided with the first aperture 33 and the second aperture 22 respectively, so that the fastening nut 30 can move with a degree of freedom of a wider angle range with respect to the screw body 10.

Figure 8:
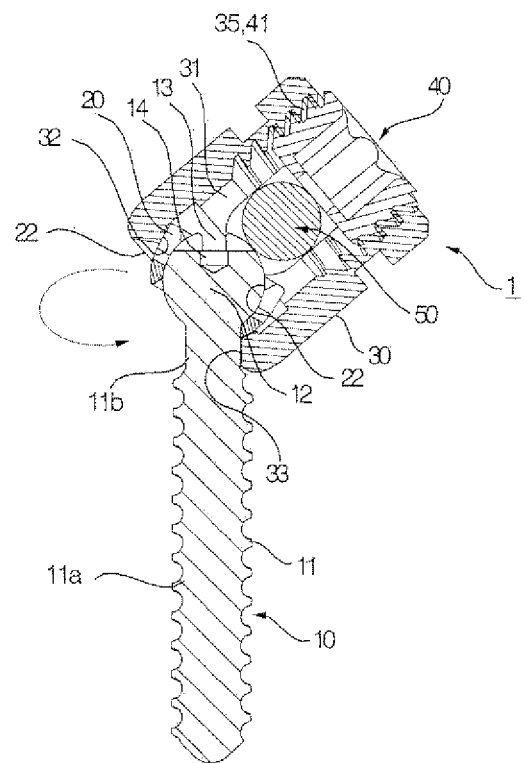
FIGS. 8 and 9 are cross sectional views for describing the operating state of the screw for fixing vertebra shown in FIG. 2.
Figure 9:
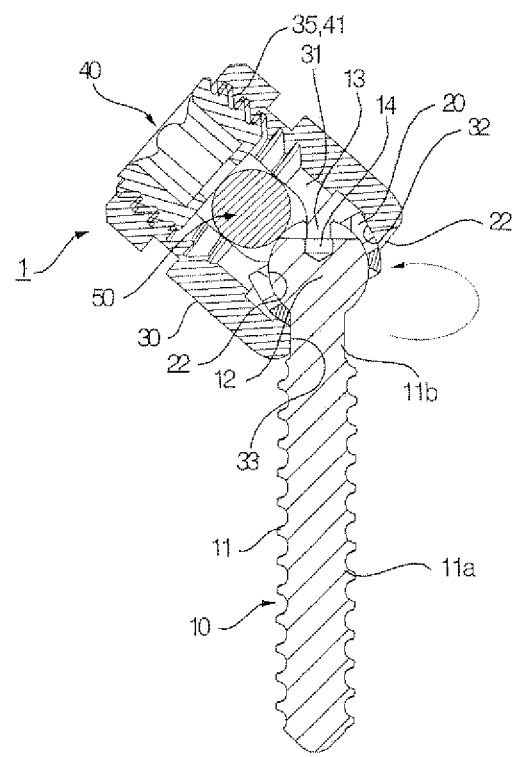

FIGS. 8 and 9 are sectional views showing the operating state of the fastening screw of the screw for fixing vertebra shown in FIG. 1.

Referring to FIGS. 8 and 9, the head portion 12 of the screw body 10 of the screw for fixing vertebra 1 according to the present embodiment is pivotally joined in sliding contact with the head seat portion 21 of the movable washer 20, and again the movable washer 20 is pivotally joined in sliding contact on the washer seat portion 32 of the fastening nut 30. Therefore, by dint of the screw for fixing vertebra, 1 of the present embodiment, the motion between the vertebras that are fixed to each other by the connecting rod 50 can be made more smoothly.

As described above, according to the screw for fixing vertebra 1 of the present embodiment, the first aperture 33 and the second aperture 22 are formed respectively in the fastening nut 30 and the movable washer 20, and the elongating portion 11*b* without a thread is formed between the thread 11*a* and the head portion 12 of the screw body 10, so that the vertebras fixed to each other by the connecting rod 50 can move with a greater degree of freedom within the maximum allowable angle range defined by the sloping face 33*a* of the first aperture 33 of the fastening nut 30.

Therefore, in some embodiments, a screw for fixing vertebra for letting a patient perform spinal motion more smoothly after a pedicle screw insertion surgery is disclosed. A head portion 12 of the screw body 10 is pivotally joined in sliding contact on the head seat portion 21 of a movable washer 20, which is again pivotally joined in sliding contact on the washer seat portion 32 of a fastening nut 30. Therefore, the fastening nut 30 can move more smoothly with respect to the screw body 10. Accordingly, the motion between the vertebras fixed to each other by the connecting rod can be made more comfortably and naturally. In addition, a first aperture 33 and a second aperture 22 are formed in the fastening nut 30 and movable washer 20 respectively, and an elongating portion 11*b* without a thread is formed between a screw portion 11*a* and the head portion 12 of the screw body 10, so that the fastening nut 30 can move with a greater degree of freedom within the maximum allowable angle range defined by the sloping face of the first aperture 33.

Although the present invention has been described in connection with the exemplary embodiments shown in the drawings, it is only illustrative. It will be understood by those skilled in the art that various modifications and equivalents can be made to the present invention. Therefore, the true technical scope of the present invention should be defined by the appended claims.

What is claimed is:

1. A screw assembly, comprising:
   a screw body having a screw portion configured to be driven into and fixed to a vertebra and a spherical head portion formed at the top end of the screw portion, the screw body having an elongating portion which elongates between a threaded portion and the head portion;
   a movable washer, which includes a head seat portion formed therein so that the head portion of the screw body is mounted thereon after the screw portion of the screw body is inserted therein, and in which the screw body is pivotally joined therein in sliding contact between the head portion and the head seat portion; wherein the movable washer has a second aperture formed with a sloping face having a length whose width gradually widens as it goes downward from the lower portion of the washer seat portion;
   a fastening nut which includes an insertion hole formed therein to insert and pass the screw body, a washer seat portion formed below the insertion hole so that the movable washer is pivotally mounted thereon in sliding contact between the movable washer and the washer seat portion, the fastening nut having a first aperture including a sloping face having a length, a rod fastening groove which extends from the upper side of the washer seat portion to the top end of the fastening nut; and, a clamping bolt which includes a male thread formed thereon to be screwed into an upper portion of the insertion hole of the fastening nut, so as to press and fix a connecting rod inserted through the rod fastening groove of the fastening nut, wherein the length of the elongating portion of the screw body is equal to the sum of a length of the sloping face of the first aperture of the fastening nut and a length of the sloping face of the second aperture of the movable washer.

2. The screw assembly according to claim 1, wherein the first aperture formed with a sloping face whose width gradually widens as it goes downward from the lower portion of the washer seat portion, and the movable washer having a head seat portion with a bottom end portion of the extending from the first aperture of the fastening nut.

3. The screw assembly according to claim 2, wherein a height of the bottom end portion of the movable washer exposed downward of the fastening nut through the first aperture is equal to the height of the first aperture.

4. The screw assembly according to claim 3, wherein the movable washer has a the second aperture of the movable washer is formed with a sloping face whose width widens gradually as it goes downward from the lower portion of the head seat portion.

5. The screw assembly according to claim 4, wherein a first tool insert groove for inserting a tool is formed in the top end portion of the head portion of the screw body, and a shaking prevention groove communicating with the first tool insert groove is formed at the center of the head portion of the screw body.

* * * * *